US006991612B2

(12) United States Patent
Scheinberg et al.

(10) Patent No.: US 6,991,612 B2
(45) Date of Patent: Jan. 31, 2006

(54) ORTHOPEDIC SPLINTS

(75) Inventors: Samuel Scheinberg, Otis, OR (US); Adrian A. Polliack, Lake Oswego, OR (US)

(73) Assignee: The Seaberg Company, Inc., Newport, OR (US)

( * ) Notice: Subject to any disclaimer, the term of this patent is extended or adjusted under 35 U.S.C. 154(b) by 0 days.

(21) Appl. No.: 10/869,130

(22) Filed: Jun. 16, 2004

(65) Prior Publication Data

US 2004/0225241 A1    Nov. 11, 2004

Related U.S. Application Data

(63) Continuation-in-part of application No. 10/357,659, filed on Feb. 3, 2003.

(51) Int. Cl.
*A61F 5/00* (2006.01)

(52) U.S. Cl. .................... 602/6; 602/5; 602/20; 602/23

(58) Field of Classification Search .................... 602/6, 602/5, 9, 12, 20, 21, 61, 64, 60, 1, 14, 17, 602/18, 19, 23; 128/877, 878, 879, 880
See application file for complete search history.

(56) References Cited

U.S. PATENT DOCUMENTS

| | | | | |
|---|---|---|---|---|
| 2,957,475 A | * | 10/1960 | Drake .......................... 602/5 |
| 3,916,884 A | * | 11/1975 | Attenburrow ................ 602/18 |
| 3,938,509 A | | 2/1976 | Barber ........................ 128/77 |
| 3,943,923 A | | 3/1976 | Scheinberg ............... 128/89 R |
| 4,161,175 A | | 7/1979 | Bentele .................... 128/87 A |
| 4,549,537 A | | 10/1985 | Ender ....................... 128/87 A |
| 4,676,233 A | * | 6/1987 | Scheinberg ................. 602/18 |
| 4,677,971 A | | 7/1987 | Lindemann ............... 128/87 R |
| 4,854,309 A | | 8/1989 | Elsey ........................ 128/87 R |
| 5,069,203 A | | 12/1991 | Anderson ................. 128/87 R |
| 5,199,941 A | | 4/1993 | Makinen ..................... 602/27 |
| 5,248,292 A | * | 9/1993 | Holland ........................ 602/6 |
| 5,348,530 A | * | 9/1994 | Grim et al. .................. 602/13 |
| 5,417,645 A | | 5/1995 | Lemmen ..................... 602/21 |
| 5,419,756 A | | 5/1995 | McConnell .................. 602/36 |
| 5,520,625 A | | 5/1996 | Malewicz .................... 602/21 |
| RE35,290 E | | 7/1996 | Druskoczi ................... 602/18 |
| 5,600,849 A | | 2/1997 | Hu ................................ 2/16 |
| 5,601,597 A | | 2/1997 | Arrowood et al. .......... 606/203 |

(Continued)

FOREIGN PATENT DOCUMENTS

GB    2337704    12/1999

*Primary Examiner*—Henry Bennett
*Assistant Examiner*—Dinnatia Doster-Greene
(74) *Attorney, Agent, or Firm*—Chernoff, Vilhauer, McClung & Stenzel, LLP

(57) ABSTRACT

An orthopedic wrist splint with an initially generally planar malleable metal core covered by a layer of synthetic foam padding material on each of its opposite sides and protected by an outer cover of fabric. In one embodiment, depending on the orientation of the splint relative to the patient, the splint provides greater or lesser firmness of support when the core is bent to conform the splint to the patient's hand, wrist, and forearm. In another embodiment, a central part of the length of the splint lacks the metal core and is flexible, so that two parts of the splint are easily used on opposite sides of an arm or ankle, with the central part comfortably bent around an elbow or a foot, and with the splint firmly supporting the limb.

19 Claims, 9 Drawing Sheets

U.S. PATENT DOCUMENTS

| | | | |
|---|---|---|---|
| 5,642,739 A * | 7/1997 | Fareed | 128/881 |
| 5,685,013 A | 11/1997 | Hausman | 2/16 |
| 5,733,249 A | 3/1998 | Katzin et al. | 602/21 |
| 5,819,312 A | 10/1998 | Snyder et al. | 2/16 |
| 5,833,636 A * | 11/1998 | Yokoi | 602/5 |
| 6,039,706 A | 3/2000 | Bolla et al. | 602/5 |
| 6,106,492 A | 8/2000 | Darcey | 602/8 |
| 6,120,472 A | 9/2000 | Singer, Jr. | 602/64 |
| 6,213,969 B1 | 4/2001 | MacMorran et al. | 602/64 |
| 6,261,253 B1 * | 7/2001 | Katzin | 602/21 |

* cited by examiner

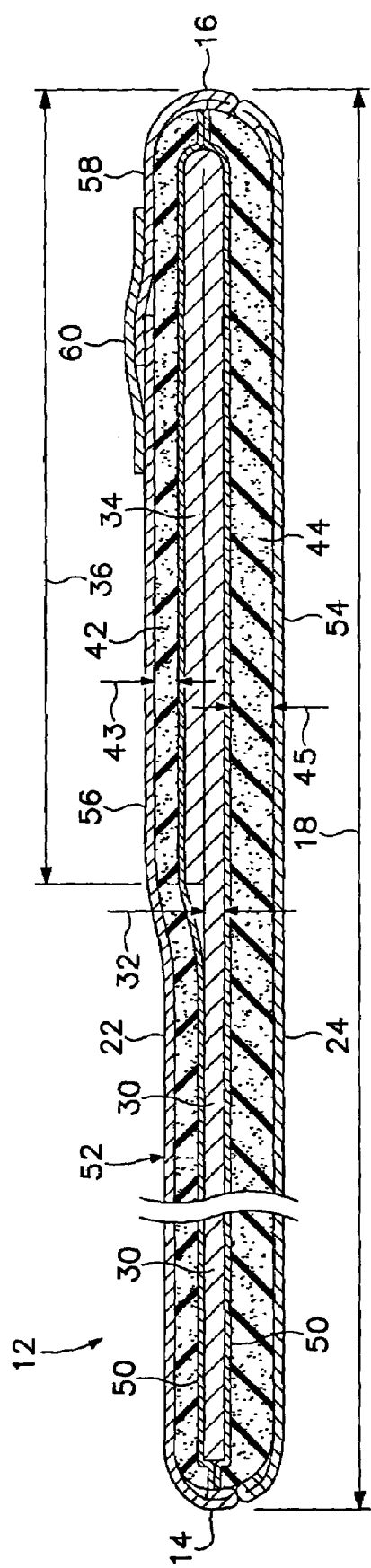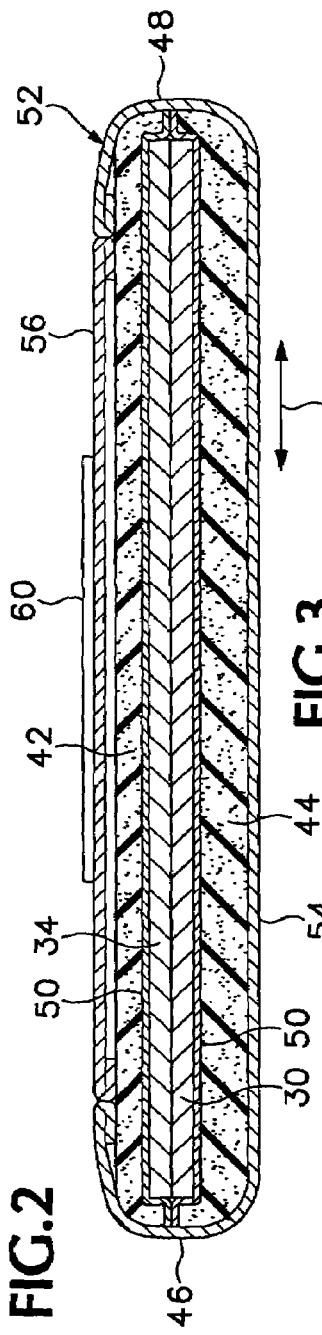
FIG.2
FIG.3
FIG.4A
FIG.4B

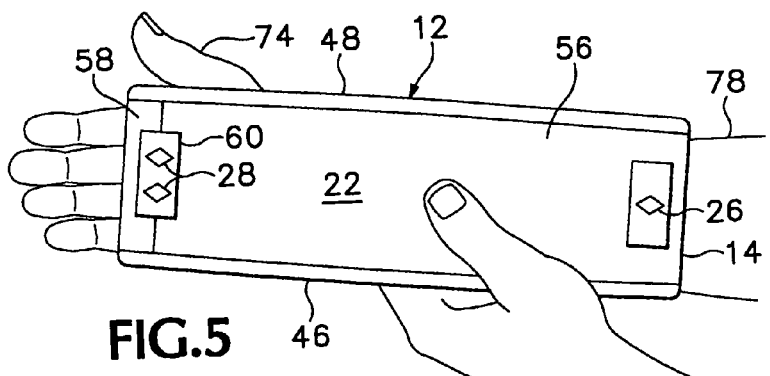
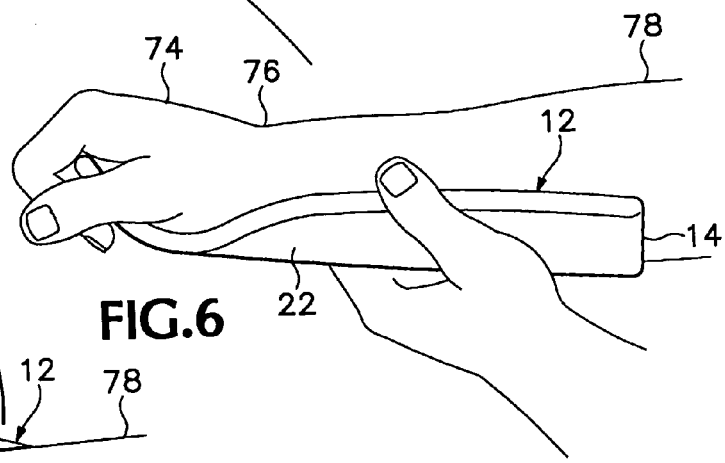
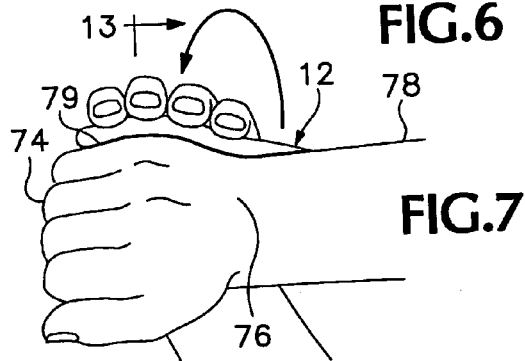
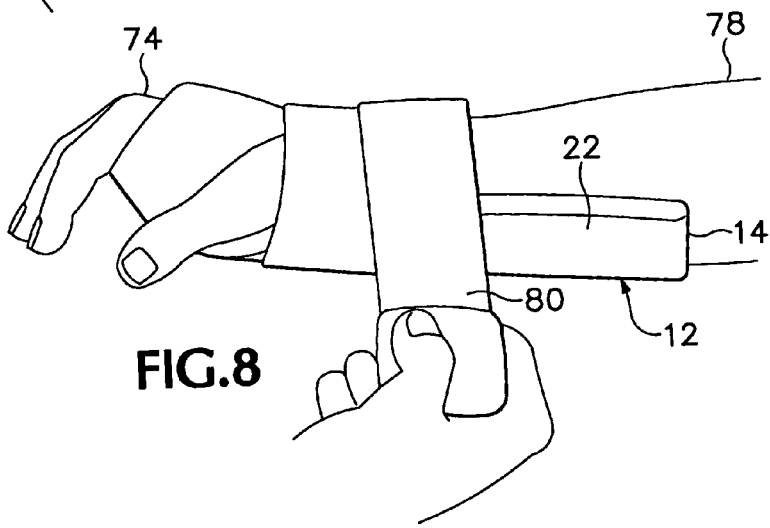

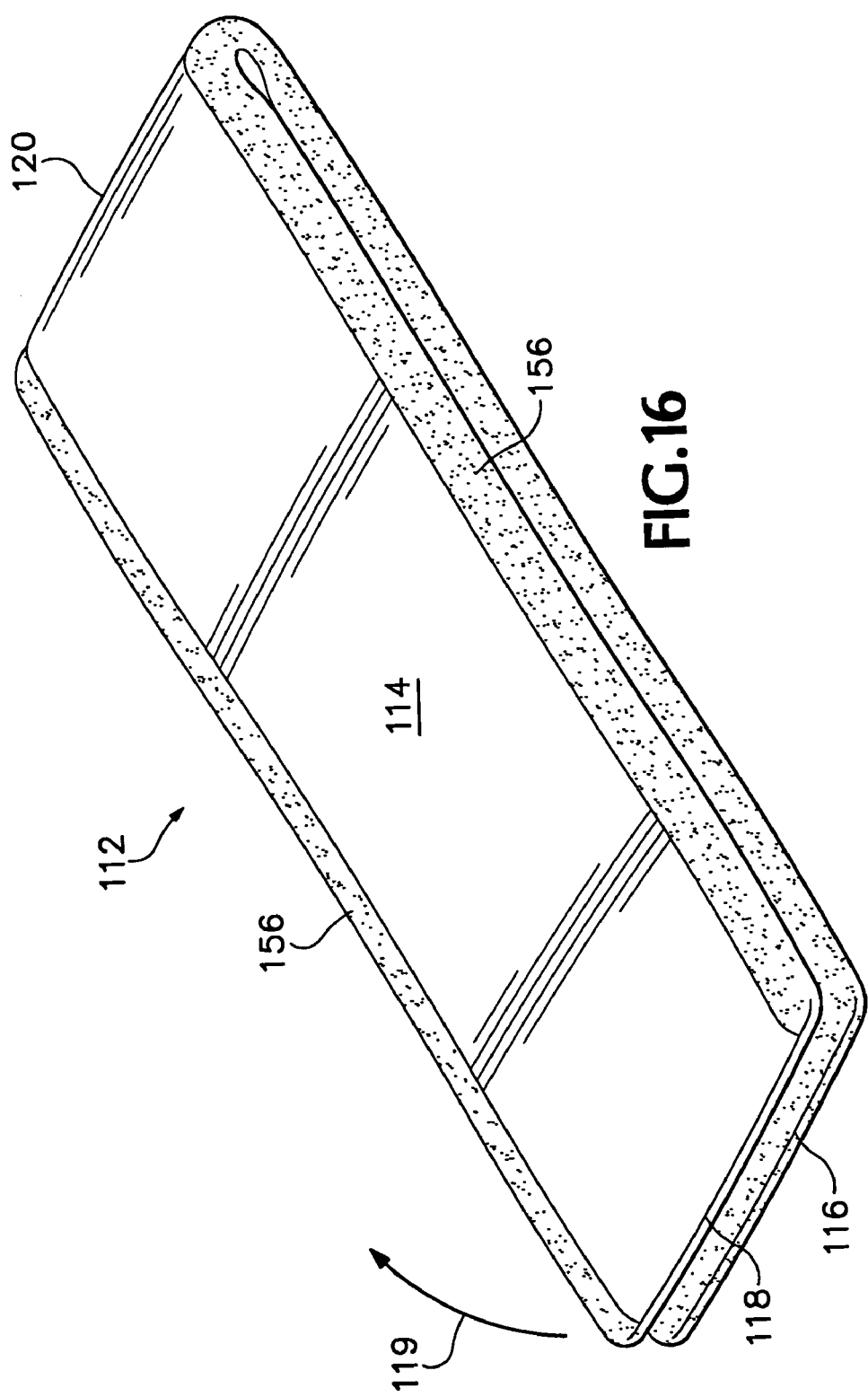

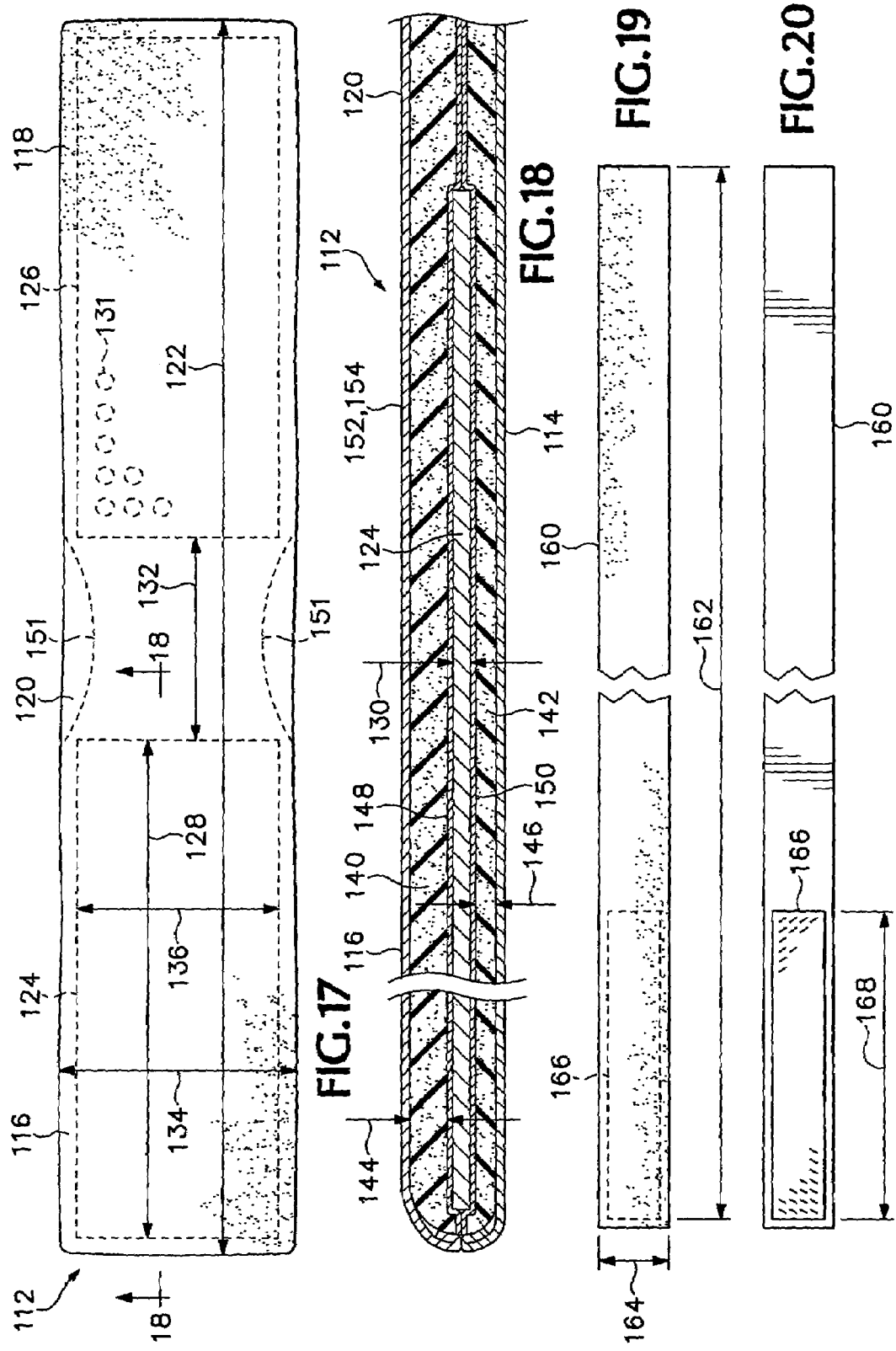

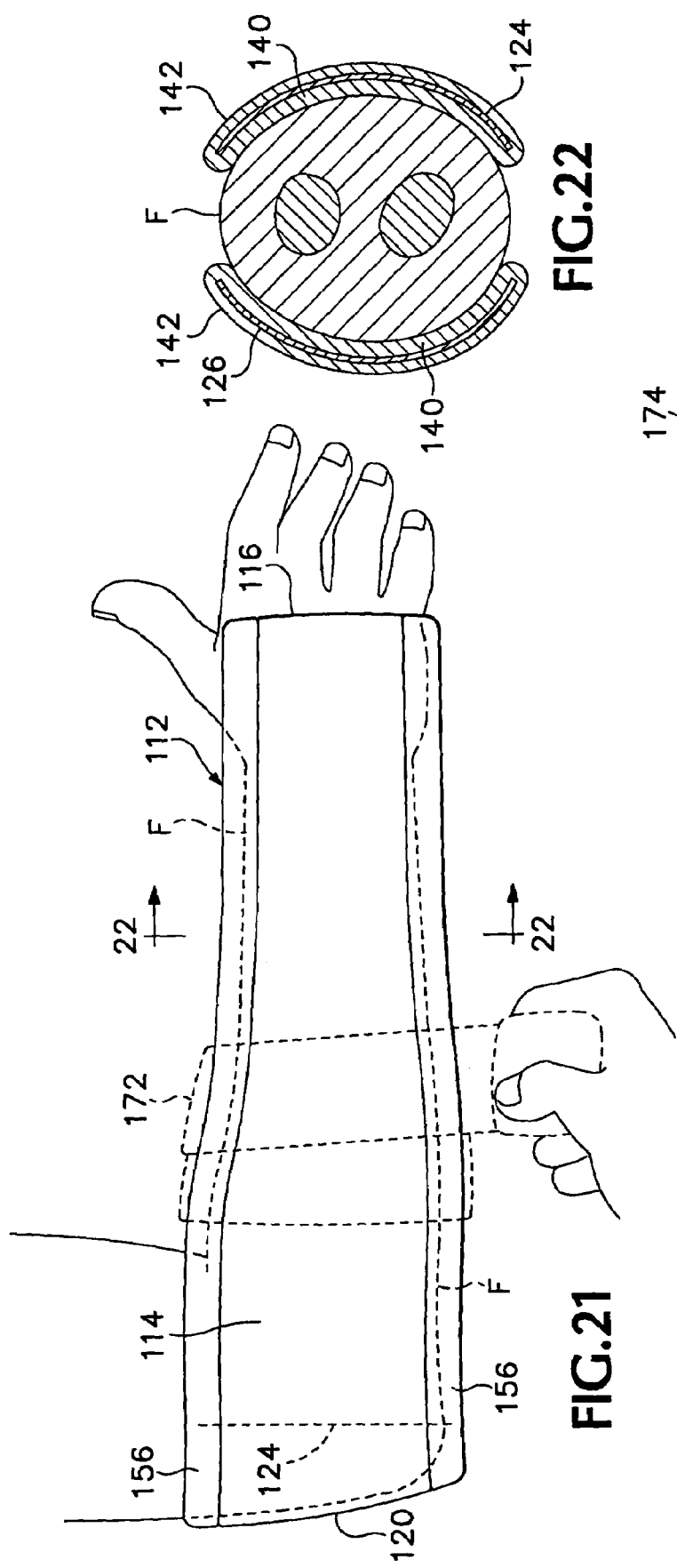
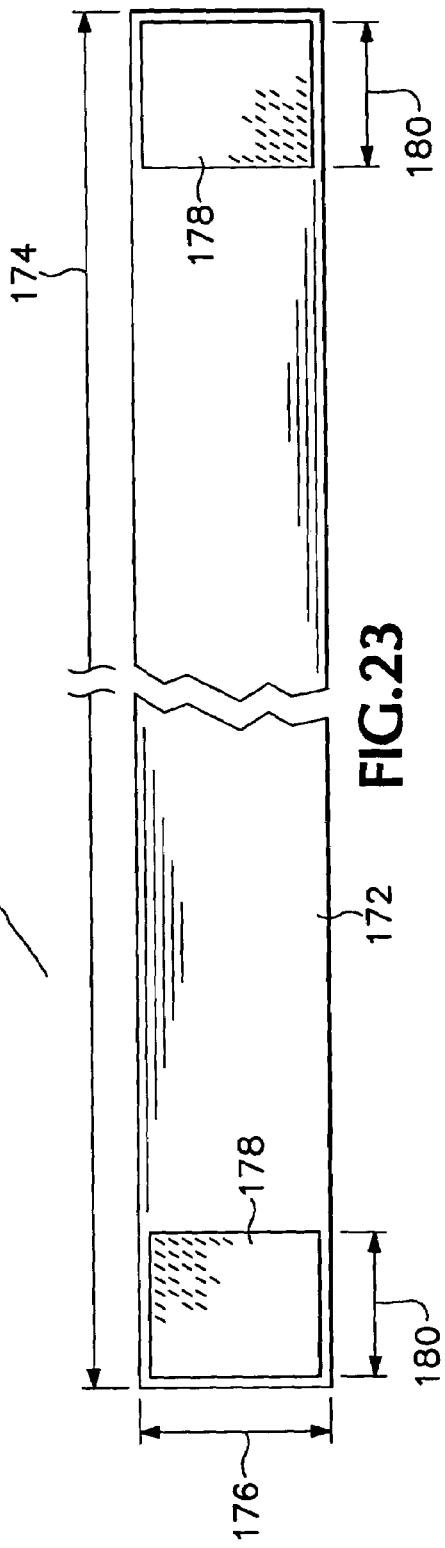

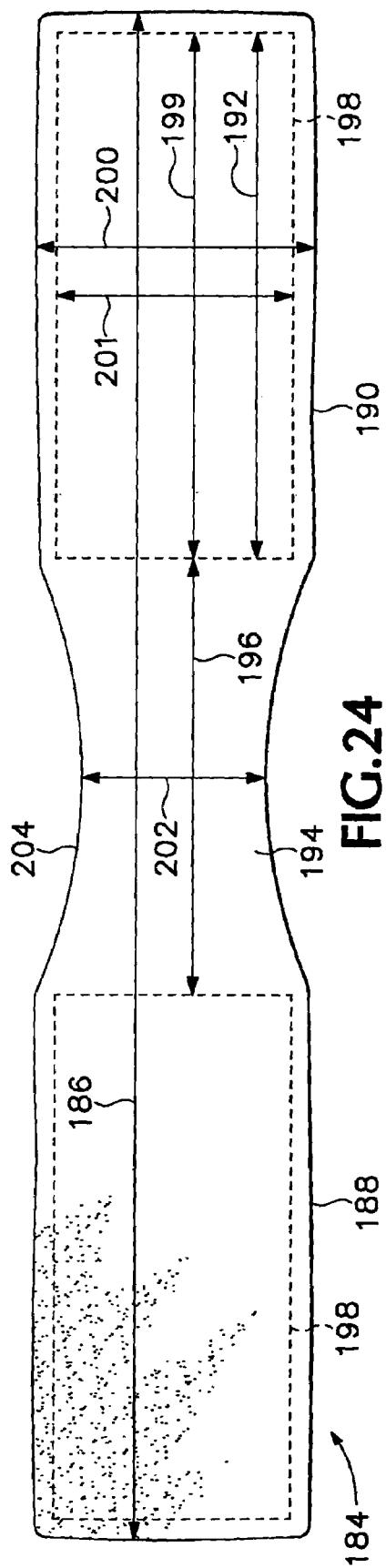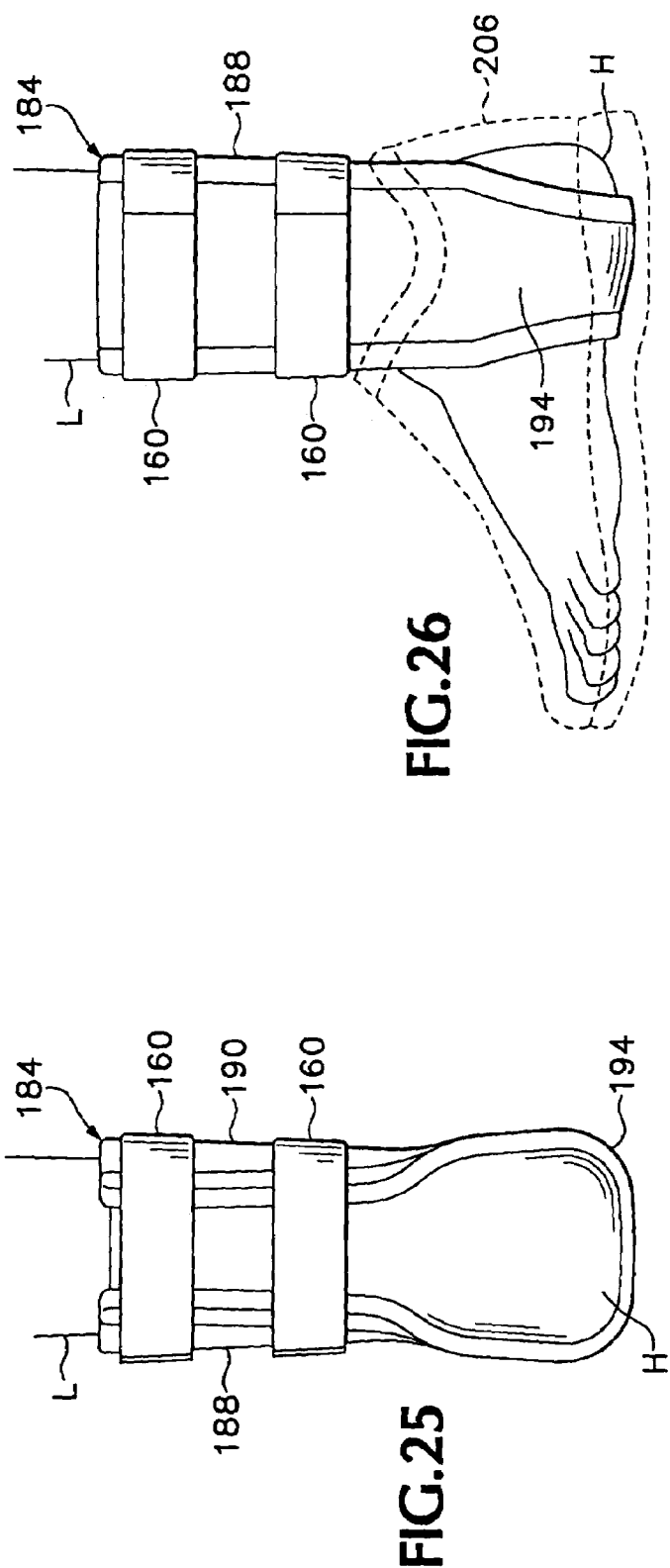
FIG. 24
FIG. 25
FIG. 26

ORTHOPEDIC SPLINTS

CROSS-REFERENCE TO RELATED APPLICATIONS

This application is a continuation-in-part of co-pending application Ser. No. 10/357,659, filed Feb. 3, 2003.

BACKGROUND OF THE INVENTION

The present invention relates to splints for immobilizing injured body members, and particularly to an improved splint that can be shaped to support a patient's hand, wrist, and forearm in comfort, and a method for its use.

Splints for use in emergency and post-operative situations are known, for example, from Scheinberg, U.S. Pat. Nos. 4,676,233 and 3,943,923, both of which teach the use of a soft metal sheet formed into a configuration that provides needed support for an injured limb. Bentele U.S. Pat. No. 4,161,175 discloses surgical splints incorporating formed sheet metal or molded plastic bases. Ender U.S. Pat. No. 4,549,537 discloses another splint based on the use of sheet aluminum material. Bolla et al. U.S. Pat. No. 6,039,706 discloses a splint using a sheet of corrugated metal as its principal supporting structure.

Health care professionals have long used splints and casts fashioned out of plaster, fiberglass, preformed metal, or molded thermoplastic materials. These splints are designed to rigidly prevent motion and once formed into position cannot be reformed, for example to accommodate swelling, without considerable difficulty. A thermosetting plastic or fiberglass-reinforced resin splint once cured cannot be reformed. If swelling is excessive, a new fiberglass or plaster splint must be applied or an instrument resembling a large pliers (often referred to as a cast bender) is used to break the plaster or fiberglass material in order to relieve the pressure caused by the swelling. A thermoplastic splint is usually rigid and requires heat in order to be reformed. Preformed metal splints are also quite rigid and difficult to bend or mold. None of the above mentioned splints once formed allow a patient to perform any significant active movement or provide variably controlled active movement.

Active movement in a joint is movement performed by the patient, as opposed to passive movement, i.e., movement performed by a physical therapist. Controlled variable active movement is active movement that can be increased or decreased according to the desire of the treating health professional. For example, it is desirable for orthopedic surgeons to vary a patient's allowable active movement during a post-operative convalescent period—i.e., the surgeon might desire less active movement during the first post-operative week and greater movement during the second post-operative week. Today, active movement is thought to be of significant value in the rehabilitation and treatment of both fractures and soft tissue conditions. For example, following an open reduction and internal fixation of a distal radial (wrist) fracture orthopedic surgeons frequently direct their patients to remove their splints several times a day for active range of motion exercises. When these splints are removed patients are at increased risk of sustaining an injury. Therefore, it is desirable to have not only an easily formable splint to accommodate post injury swelling, but a splint capable of allowing variable degrees of active movement while remaining in place.

Where a person has received an injury to an ankle or forearm that needs to be immobilized, previously known conformable splint devices for use as disclosed in Scheinberg et al. U.S. Pat. No. 3,943,923 and Scheinberg U.S. Pat. No. 4,676,233, available from The Seaberg Company, Inc. of Newport, Oreg. under the trademark SAM® SPLINT have been widely used. The lack of precise conformation of such splints to the limb allows unwanted rotation and lateral movement, which, in turn, could affect injuries occurring anywhere along the length of the encompassed limb.

In the case of an ankle or lower leg injury, it can be desirable to use an injured person's shoe or boot to provide some support and aid in immobilizing the injured parts, but the bulk resulting from use of the devices according to the mentioned Scheinberg U.S. patents directly on a person's ankle usually prevents replacement of a shoe or boot. In some cases, therefore, such a splint is placed around the outside and under the heel of a person's boot or shoe where it provides some useful support, but is less than ideal.

What is desired, then, is a splint that can readily be used to support an injured forearm or ankle, and which is not only more effective in controlling rotation and lateral movement, but more easily applied than previously available splints, and which can be easily used without causing discomfort, and which is small enough to permit replacement of a person's shoe or boot over a splinted ankle.

SUMMARY OF THE INVENTION

The present invention provides an answer to some of the shortcomings of the previously available splints, by providing a splint that can readily and precisely conform to the elbow and ankle, that is conveniently portable and storable in a planar configuration prior to preparation for use with a particular patient, and which can provide comfortable support for a patient's hand, wrist, forearm and ankle.

In a first preferred embodiment of the invention, such a splint has a body that includes an elongate flat supportive member, or core, of malleable metal that is more supportive at one end of the splint than at the other end. The same splint then can be used depending on its orientation, to provide either a greater or lesser amount of firmness of support for a patient's wrist, varying the patient's ability to perform active movements.

A layer of padding material is attached to each side of the core, and in one preferred embodiment of the invention an outer cover provides additional comfort and carries indicia to identify the amount of support provided by each end of the splint.

In one preferred embodiment of the invention, the padding material on a skin contact surface, or the splint surface directly adjacent to the skin, referred to herein as the closer face of the splint, may preferably be of open-cell synthetic polymeric foam material, and the outer cover on that closer face of the splint is preferably of absorbent fabric that is open to passage of moisture and vapors, so as to maintain the patient's comfort with the splint in contact with the patient's skin.

In one preferred embodiment of the invention, a portion of the outer cover located on the opposite the splint surface not in contact with the skin, the farther face of the splint, is of material adapted to be engaged by the hook-carrying fastener portion of a hook-and-loop fastener system in order to facilitate the attachment of straps used to encircle the patient's hand, wrist, and arm to hold the splint in place.

As another aspect of the invention, a pair of elongate supportive members of malleable metal are covered by a layer of padding material and are aligned with each other end-to-end but separated by a distance, and are joined together by a flexible connecting material which may be an extension of the padding materials. The soft padding material interconnecting the two supportive members remains easily flexible to conform comfortably and precisely around the patient's elbow without creating uncomfortable bulk, and allows the firmer, metal supportive members to be shaped to conform to opposite sides of a patient's forearm.

Similarly, such a flexible interconnecting portion extends around and beneath a patient's heel with ease in conforming to the heel comparable to that of the best previously available ankle splint devices, and provides padded and comfortable support with little or no bulk, for an injured ankle while allowing a boot to be placed over the splint.

In a preferred embodiment of this aspect of the invention, the padding material associated with the supportive members is similar in material and thickness to that used for a wrist splint.

In a preferred embodiment of this aspect of the invention, an outer cover of material that may be similar to that of the outer cover of the wrist splint is utilized and includes material adapted to be engaged by the hook-carrying fastener portion of a hook-and-loop fastener system in order to facilitate the attachment of straps to encircle the patient's forearm or ankle and lower leg.

The foregoing and other objectives, features, and advantages of the invention will be more readily understood upon consideration of the following detailed description of the invention, taken in conjunction with the accompanying drawings.

BRIEF DESCRIPTION OF THE SEVERAL DRAWINGS

FIG. 2 is a sectional view of the splint shown in FIG. 1 taken along line 2—2.

FIG. 3 is a sectional view taken along line 3—3 of FIG. 1.

FIG. 4A is a side elevational view of an alternative core portion of a splint similar to that shown in FIGS. 1 and 2, taken in the direction indicated by line 2—2 in FIG. 1.

FIG. 4B is a view similar to that of FIG. 4A showing another alternative core member for an orthopedic splint such as that shown in FIGS. 1 and 2.

FIG. 5 is a pictorial view showing a splint such as the one shown in FIG. 1 adjacent the volar side of a patient's hand, wrist, and forearm before being shaped to fit the patient.

FIG. 6 is a pictorial view showing the splint shown in FIG. 5 in the process of being shaped to the configuration necessary for use.

FIG. 7 is a pictorial view showing how the splint shown in FIGS. 5 and 6 is bent further to conform to the ulnar side of a patient's hand.

FIG. 8 is a pictorial view showing the application of an elastic wrap to secure the splint shown in FIGS. 5–7 to the patient's hand, wrist and arm.

FIG. 16 is a perspective view of a splint according to the invention and shown in a preferred configuration for being packaged.

FIG. 17 is a plan view of the splint shown in FIG. 16 extended into a flat configuration and to its full length, in order to more clearly depict the structures of the splint.

FIG. 18 is a foreshortened section view at an enlarged scale taken along line 18—18 in FIG. 17, showing the arrangement of different portions of the splint shown in FIGS. 16 and 17.

FIG. 19 is a plan view of a strap intended to be utilized with the splint shown in FIGS. 16–18, taken from a first side.

FIG. 20 is a plan view of the strap shown in FIG. 19, taken from its opposite side.

FIG. 21 is a view of a patient's arm and showing the splint shown in FIGS. 16–18 applied around the patient's elbow and held in place by an elastic bandage such as that shown in FIG. 23 to retain the splint on the patient's forearm.

FIG. 22 is a simplified sectional view of the arrangement of the splint shown in FIG. 21, taken along line 22—22 in FIG. 21.

FIG. 23 is a foreshortened plan view of another strap which might be used in place of the strap shown in FIGS. 19 and 20.

FIG. 24 is a plan view of a splint slightly different in form from that shown in FIGS. 16–18 and intended to be used on a patient's ankle.

FIG. 25 is a view of the splint shown in FIG. 24 in place to support a patient's ankle and lower leg.

FIG. 26 is a side view of the splint shown in FIG. 24 in place with the patient's boot also in place to provide support for an ankle.

DETAILED DESCRIPTION OF PREFERRED EMBODIMENTS

Figure 1:
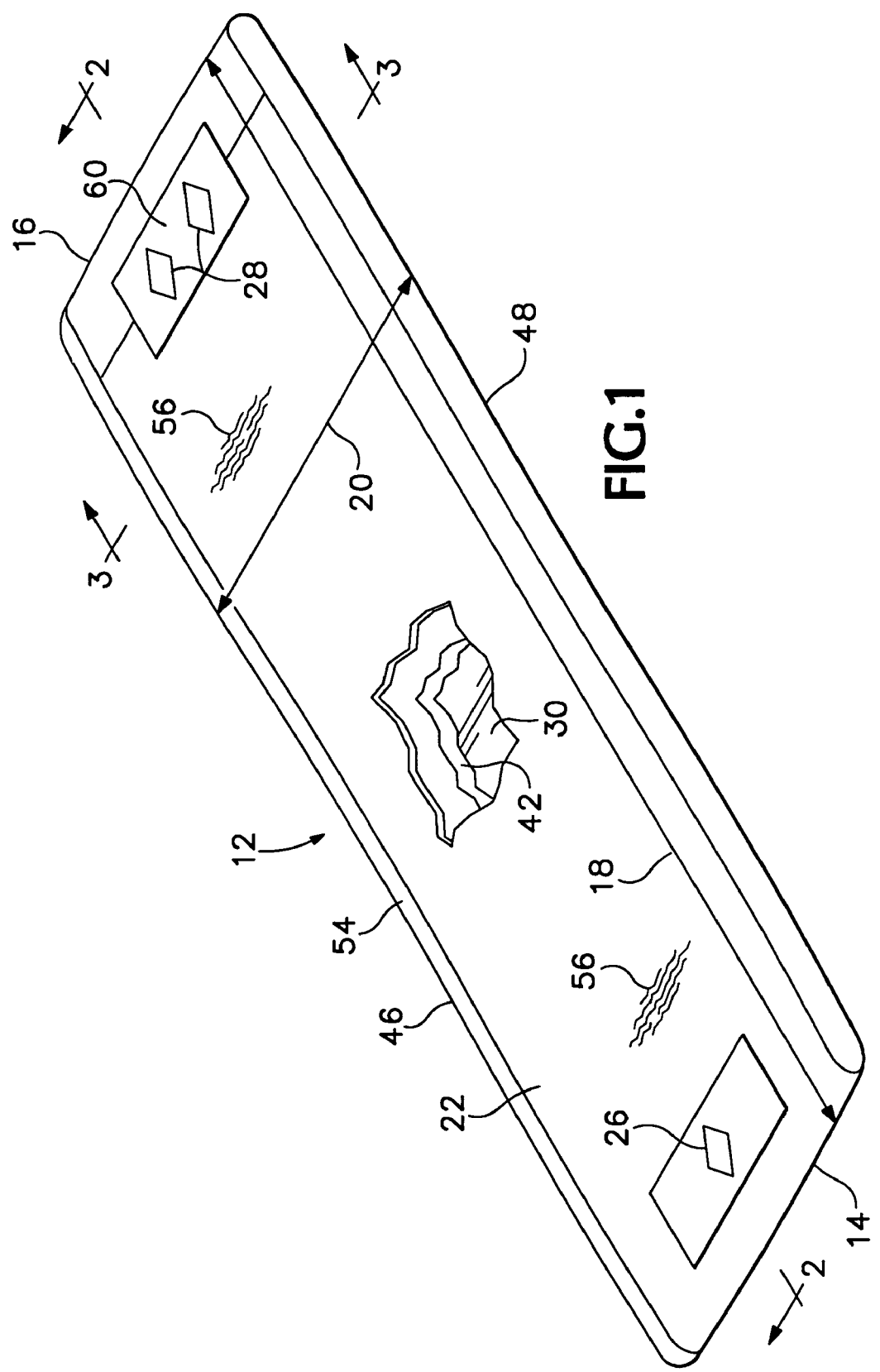
FIG. 1 is an isometric view of an orthopedic splint according to the present invention in a storage configuration.

Referring now to the drawings which form a part of the disclosure herein, in FIGS. 1 and 2 a splint 12 which is a first preferred embodiment of the present invention is shown in a generally planar configuration in which the splint is manufactured and is usually packaged for shipment and for storage prior to its use. A body of the splint 12 has a first end 14 and an opposite second end 16 defining a length 18 that is greater than the width 20. For example, the length 18 may be twelve to fifteen inches and the width 20 may be in the range of four to six inches, and preferably about 4½ inches for a splint 12 intended for use to support the wrist of an adult.

The body of the splint has a skin contact, or closer face 24, intended to be placed in contact with a patient's skin or wound dressing, and shown in FIG. 2, but facing downward in FIG. 1. An opposite or farther face 22 of the splint facing upward, in FIG. 1, and normally faces outward, away from a patient's skin when the splint 12 is in use. The designations as closer and farther faces 24 and 22 thus refer to the proper orientation of the splint 12 with respect to a person's arm, wrist, and hand when the splint 12 is in use.

Identifying indicia are provided on the face 22 of the splint 12, in the form of, for example, a single diamond 26 displayed on the farther face 22 adjacent the first end 14 of the splint 12 and a pair of diamonds 28 or other distinguishable marking provided on the farther face 22 adjacent the second end 16 of the splint 12. The indicia 26 and 28 distinguish the first end 14 from the second end 16, because the construction of the splint, as will be explained presently, provides support for a patient's hand and wrist with a first amount of firmness provided by the structure at the first end 14 of the splint 12 and with a second, greater, amount of firmness provided by the structure of the second end 16 of the splint 12.

The splint 12 as shown in FIGS. 1–3 has a core 30 of malleable metal in the form of a flat sheet whose dimensions are slightly smaller than the length 18 and width 20 of the splint 12.

At the second end 16 of the splint 12, the core 30 includes a thicker portion 34 having a length 36 preferably in the range of about 3 to 6 inches, and preferably of about 4.5 inches, for a splint whose length 20 is in the range of about 9–15 inches, in which the core 30 has a greater thickness, in order for the splint to provide greater firmness. The greater thickness may be provided by folding the aluminum sheet material back upon itself adjacent the second end 16. The length 36 of the thicker portion 34 is thus long enough to provide support for the wrist 76 of an adult. As a result of the greater thickness, the thicker portion 34 of the core 30 adjacent the second end 16 of the splint 12 is stiffer than the portion of the core 30 adjacent the first end 14 of the splint 12. Preferably the core 30 is of nearly pure aluminum such as Aluminum Association Type 1XXX aluminum, and preferably Type 1145 aluminum sheet material (99.45% pure) having a thickness 32 in the range of 0.008 inch-0.025 inch, and preferably having a thickness of about 0.016 inch. Preferably the metal is annealed to a dead soft or "O" temper. Bending the aluminum core 30 during the process of adjusting the splint 12 to conform to a patient creates a curved cross-section that increases the rigidity of the splint, i.e., makes it more resistant to bending.

A farther side layer 42 of padding material and a closer side layer 44 of padding material envelop the core 30 and extend slightly beyond it at each of the first and second ends 14 and 16 and along the opposite longitudinal lateral margins 46 and 48 of the splint 12. The farther side and closer side layers 42 and 48 of padding material are attached to the respective opposite closer and farther sides of core 30 and to each other by respective layers 50 of adhesive material which also interconnects the farther side layer 42 of padding material to the closer side layer 44 of padding material along the margins adjacent the opposite ends 14 and 16 and opposite lateral margins 46 and 48 of the splint 12. Preferably the layers 42 and 44 of padding material extend beyond the margins of the core 30 a distance sufficient to provide comfortable padding. For example, in a splint 12 whose width 20 is 4½ inches the core 30 is 3.9 inches wide, and the layers 42 and 44 of padding material may extend about ³⁄₁₆ inch beyond the core 30 at each of the first and second ends 14 and 16 and an ⅛ inch beyond the core 30 along each of the lateral margins 46 and 48.

A layer of pressure-sensitive adhesive material, which may be acrylic based, is provided on the surface of each of the layers of polymeric foam material of the farther side layer 42 and the closer side layer 44, protected by a peel-off liner which is removed when the layers 42 and 44 of padding material are attached to the core. This adhesive material becomes the layer 50 mentioned above, in the manufacture of the splint 12.

Enclosing the core 30 and the layers 42 and 44 of padding material is an outer cover 52 of textile fabric. Preferably, the outer cover 52 is made of two different types of fabric, with a first, or closer face part 54 of the outer cover 52 being located on and defining the closer face 24 of the splint 12, and preferably extending around the lateral margins 46 and 48 and onto the farther face 22 a short distance, as seen best in FIGS. 1 and 3. A farther face part 56 of the outer cover 52 is preferably of a different fabric.

The farther side layer 42 of padding material has a thickness 43 preferably in the range of ¹⁄₁₆ inch to ¼ inch, and the thickness 43 is most preferably ⅛ inch. The farther side layer 42 of padding material should be of a somewhat resiliently compressible or elastomeric material, and may be of a polymeric foam such as a closed cell microcellular low density expanded polyethylene available from Voltek Division of Sakisui American Corporation as its Volara Type A foam, with a layer of a flexible pressure-sensitive adhesive material already applied to one side of the foam to serve as the layer of adhesive 50.

Such foam material used as the farther side layer 42 preferably has a density of at least about 1.5 lbs. per cubic foot and preferably at least 2.0 lbs. per cubic foot. Greater densities, up to at least about 4 lbs. per cubic foot are desirable, but are considerably more expensive.

The closer side layer 44 of padding material in a preferred embodiment of the splint 12 has a thickness 45 of about ¼ inch, although a thickness 45 in the range of ⅛ inch to ⅜ inch is acceptable. The closer side layer 44 of padding material should also be somewhat resiliently compressible, and is preferably porous. Therefore, the layer 44 is preferably of open-cell polymeric foam, such as a polyurethane foam, with an applied layer of flexible pressure sensitive adhesive. An acceptable density for such foam material is 1.0–4.0 lbs. per cubic foot, with 1.5 lbs.–3.0 lbs. per cubic foot being preferred. An indentation load deflection of about 75 is preferred, but any value in the range of 25 to 150 is acceptable, to provide sufficient firmness yet be comfortable. The open-cell construction of the closer side layer 44 of padding material allows sufficient circulation of air, to cool and to dissipate evaporation from the skin of a patient using the splint 12, in order to provide ample comfort for a patient using the splint 12. One acceptable material for the closer side layer 44 is available from Foamex, of Compton, Calif., as its Foam Grade F 145 44 F.6 FA 44145-304.

Preferably, the closer face part 54 of the outer cover 52 is made of a soft, absorbent fabric with a significant amount of elasticity in at least the transverse direction, indicated by the arrow 55 in FIG. 3. For example, a brushed terrycloth or boucle fleece of 65 percent polyester and 35 percent rayon fiber of 100 denier yarn, available from Eclat Textile Co. Ltd. of City of Industry, Calif. as its product number 1206D performs well for absorbing moisture and exudate from a patient's skin. Preferably, such a cloth is a low loop, tightly knitted material, brushed to provide a soft and slightly matted surface which is absorbent and not abrasive, so that the splint 12 can be used comfortably in direct contact with the patient's skin.

The elasticity of the fabric of the closer face part 54 of the outer cover 52 allows the closer side layer 44 of padding material to conform easily to a patient's hand, wrist, and arm without the fabric of the closer face part 56 being pulled free from the closer side layer 44 of padding material when it is compressed irregularly by conforming to the shape of the patient's hand, wrist, and forearm.

The farther face part 56 of the outer cover 52, located on and defining a part of the farther face 22, may be of a material which is receptive to the hooked material portion of a hook-and-loop fastening material such as that commonly known under the trademark Velcro® or an equivalent "thistle-cloth" fastener material. Preferably the fabric of the farther face part 56 is significantly less elastic than the fabric of the closer face part 54, in order better to resist separating from the foam material of the farther side layer 42 of padding material when such a hooked fastener material is disconnected from the farther face part 56 of the outer cover 52. The farther face part 56 of the outer cover 52 extends from the first end 14 of the splint toward the second end 16, and extends over most of the width 20 of the splint 12, from one to the other of the margins of the closer face part 54 of the outer cover 52, as shown in FIGS. 1 and 3. Adjacent the second end 16 of the splint, a small piece 58 of the material of the farther face part 56 may be attached to the material of the closer face part 54 at the second end 16, to extend toward the first end 14 of the splint, slightly overlapping a portion of the main piece of the farther face part 56 to leave a slot at the second end 16 through which the core 30 and layers 42 and 44 of padding material may be inserted into the outer cover 52. Thereafter, a label 60 including indicia such as the previously mentioned pair of diamonds 28 is fastened in place, preferably by a heat-activated adhesive, to secure the outer cover 52. A label including the indicia 26 may also be attached in the same manner. A suitable material for the farther face part 56 of the outer cover 52 is a brushed nylon tricot such as is available from the Fabrite Laminating Corporation of Woodridge, N.J. as its style 5437 material, which is a warp knit fabric of 32 gauge, using 40 denier yarn to produce cloth having a weight of 2.04 ounces per square yard and a finished thickness of 0.035 inch. This cloth provides ample protection for the farther side layer 42 of padding material and may be of a kind which can receive and be engaged by the hook portion of a hook-and-loop fastener material appropriate for fastening straps to attach the splint 12 to a patient's arm 78. The material is stable enough in size not to stretch excessively when the hooked fastener material is removed. As a result, removal of the fastener materials to disconnect straps from the splint does not unduly tend to separate the material from the farther side layer 42 of padding material. The outer cover 52 may be attached to the adjacent surfaces of the layers 42 and 44 of padding material by the use of a layer of fusible heat-activated fabric adhesive, activated after the core 30 and layers of padding material 42 and 44 have been placed within the outer cover 52, or by a suitable, sprayable adhesive. Preferred fusible fabric adhesives are available from Freudenberg Nonwovens, of Durham, N.C., under the trademark Pellon®, as its product number 807 Wonder-Web™ fusible web and its product number 725 heavy-duty Wonder-Under® fusible web. The web of fusible adhesive is porous and once activated continues to permit free movement of moisture and vapor through the outer cover and the open-cell material of the closer side layer 44 of padding material.

Referring to FIGS. 4A and 4B, instead of the core 30 of sheet aluminum of which a portion 34 is folded back as shown in FIG. 2, a core 30' may be of aluminum formed, possibly by extrusion, to include a first portion 62 corresponding to the single thickness portion of the core 30 shown in FIG. 2 for the first end 14 of the splint 12, a thicker second portion 64, with a thickness generally corresponding with the doubled portion 34 of the core 30 for the second end 16 of the splint 12, and a tapered transitional portion 66. The thicker part 64 thus provides the desired greater firmness for the second end 16 of a splint 12 including the core 30'.

Alternatively, as shown in FIG. 4B, a core 30" may be uniformly and gradually tapered from a thinner end 68 to a thicker end 70, to provide greater firmness at the second end 16 of a splint 12 including the core 30" with its thicker end 70 located at the second end 16.

The splint 12 is prepared and used as depicted in FIGS. 5, 6, 7, and 8 in order to provide a desired level of support for an injured patient's hand 74, wrist 76, or forearm 78. If a moderate degree of immobilization and support is desired, the first end 14 of the splint 12, identifiable by the single diamond 26 or other indicium, is placed alongside the patient's hand, with the second end 16 extending toward the patient's elbow. Alternatively, if a greater degree of support and immobilization of the wrist and hand is desired, the second end 16 is placed adjacent to the hand 74, as shown in FIG. 5, while the first end 14 is placed alongside the patient's forearm 78. In either case the closer face 24 of the splint 12 should be directed toward the volar side of the patient's arm, usually in direct contact therewith.

In order to provide the required amount of support, the splint 12 must be shaped to conform to the patient's hand 74, wrist 76, and forearm 78. This is accomplished manually by the attending medical personnel, by first bending the splint 12 to conform generally to his or her own wrist and hand. The splint 12 is placed with the chosen end 14 or 16 nearer the patient's hand, and with the distal farther face 22 directed away from the hand 74 and forearm 78, as shown in FIG. 5, and the attending medical professional pushes on the splint 12, shaping it to conform roughly to his or her arm, as illustrated in FIG. 6. This results in the core 30 bending to assume and retain the required shape. The end portion 14 or 16 of the splint 12 adjacent the ulnar side 79 of the hand 74 is also bent upward around the hand 74 as indicated by the arrow in FIG. 7, to provide additional support and fit smoothly.

The attending person can then adjust the shape of the splint 12 to fit the patient more precisely by pushing with the thumbs against the closer face 24 while the fingers press on the farther face 22 of the splint 12. The end 14 or 76 of the splint 12 is that located within the patient's hand 74 may also be bent downward in the form of a small roll, if desired, to support the patient's fingers in a comfortable attitude, preferably using a splint 12 whose length 18 is ample. The relatively thin and firm padding material of the farther side layer 42 enables the attending person to feel the shape to which the core 30 is being bent and allows him or her to manipulate the core 30 precisely to conform as desired to the patient's hand 74, wrist 76, and arm 78. Since the core 30 is preferably annealed to be deadsoft for initial manufacture of the splint, it is initially easy to bend the core into the desired form. The required form of the splint 12 has a bending curved cross-section that provides improved rigidity by acting structurally as a "C"-shaped channel.

Once the shape of the splint 12 has been properly adjusted to fit the patient, the splint is put into place as shown in FIG. 8, with the closer face 24 of the splint facing toward the volar aspect of the patient. The splint 12 is secured in place by wrapping the patient's hand 74, wrist 76, and arm 78, and the splint 12 with an elastic bandage 80 as shown in FIG. 8.

Figure 9:
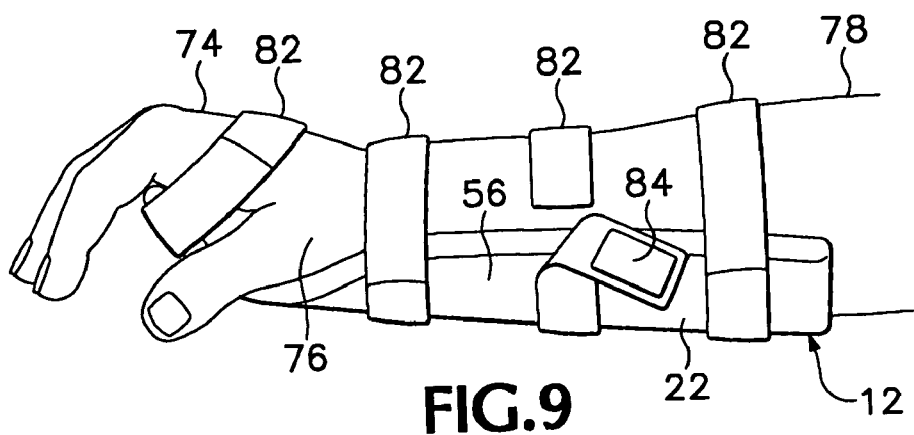
FIG. 9 is a view similar to that of FIG. 8, but showing the use of straps fastened by hook-and-loop fasteners to secure the splint to a patient's hand and arm.

Alternatively, as shown in FIG. 9, the splint 12 may be held in place by wrapping it with flexible straps 82 provided with hook-and-loop fasteners. Patches 84 of the hook portion of such hook-and-loop fastener material may be engaged in the material of the farther face part 56 of the outer cover 52 as shown in FIG. 9. Because of the nature of the fabric preferably used as the farther face part 56 of the outer cover 52 removal of the fastener material, as for adjusting the shape 82, does not significantly degrade the material of the farther face part 56 or pull it apart from the underlying farther side layer 42 of padding material.

Figure 10:
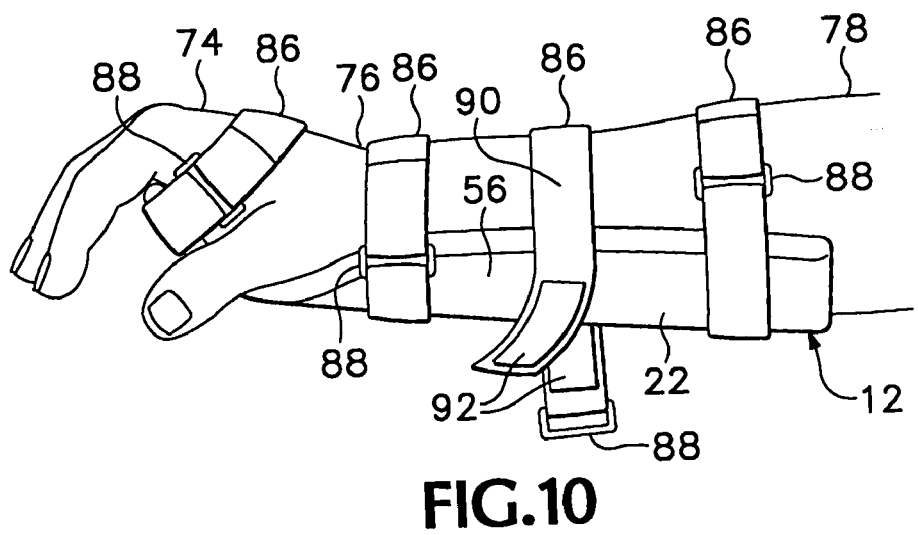
FIG. 10 is a view similar to FIG. 9, but showing the use of straps equipped with D-rings and hook-and-loop fasteners to secure the splint to a patient's arm.

Alternatively, as shown in FIG. 10 flexible separate straps 86 equipped with D-rings 88 and hook-and-loop fastener materials 90 and 92 may be placed around the patient's hand 74, wrist 76, and arm 78 and the splint 12, and if desired the hooked portion 92 of the fastener material may be engaged with the fabric of the farther face part 56 of the outer cover 52.

Figure 11:
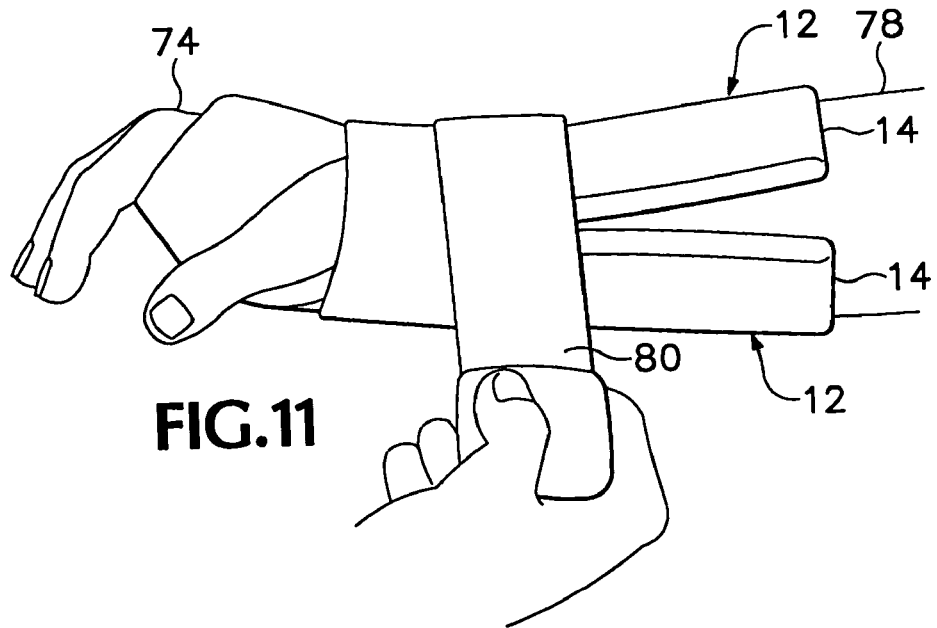
FIG. 11 is a view showing the use of a pair of splints such as that shown in FIGS. 1 and 2 in a clam-shell arrangement on a patient's wrist and arm.

As mentioned above, use of the splint 12 with the second end 16 adjacent the patient's hand 74 and wrist 78 gives greater support than use of the splint 12 with the first end 14 adjacent the hand 74 and wrist 76. In a situation where maximum immobilization of a patient's hand 74 and wrist 76 is required, a pair of splints 12 may be applied simultaneously to both the volar and dorsal sides of the patient's arm 78, as shown in FIG. 11. The two splints 12 are both shaped separately to conform to their respective intended positions and then both are secured to the patient in generally the same manner described above with respect to a single splint 12.

Figure 12:
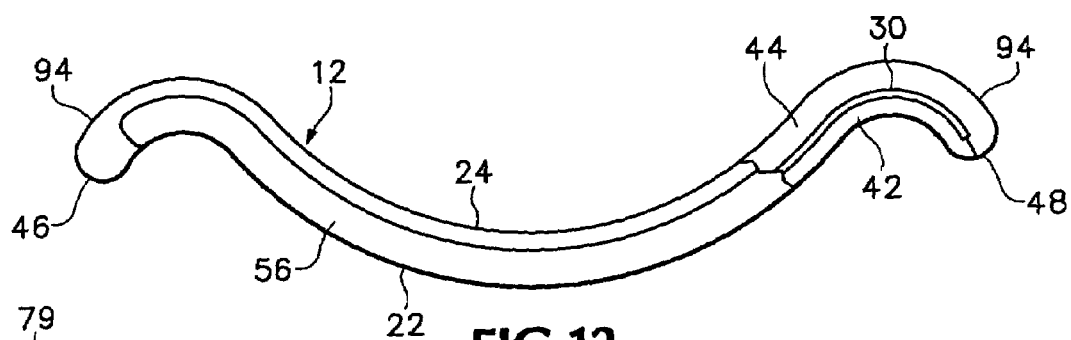
FIG. 12 is a partially cutaway end view of a splint such as that a shown in FIGS. 1–3, showing one way of forming the splint to provide additional stiffness.
Figure 13:
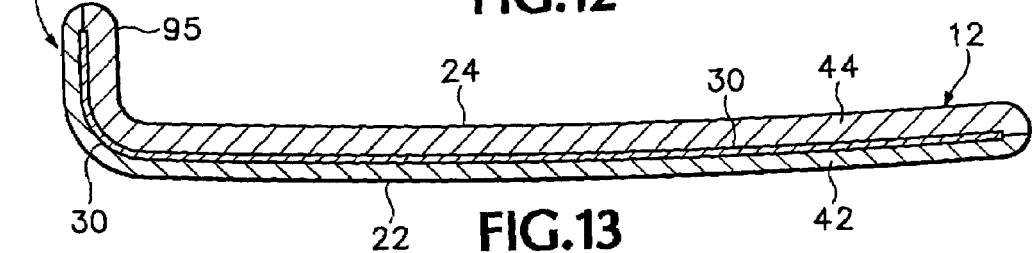
FIG. 13 is a sectional view taken along line 13—13 of FIG. 7.

In some cases, it may be desired to provide additional stiffness in the portion of the splint 12 along the patient's arm 78 by bending the splint outward to form side flanges 94 along the side margins 46 and 48 as shown in cross-section view in FIG. 12. The degree of stiffness in either end 14 or 16 of the splint can be varied most easily by folding such a portion of the splint. It is desirable in particular to bend a portion along the lateral margin 46 or 48 which is to be located on the ulnar, or little finger side of the patient's wrist 76 and forearm 78 into the form of a flange 95 along the ulnar side 79, as shown in FIGS. 7 and 13, to provide added stiffness to the splint 12 and thus provide additional firmness of support, in direct proportion to the length and depth of the portion thus formed into a flange 95.

Figure 14:
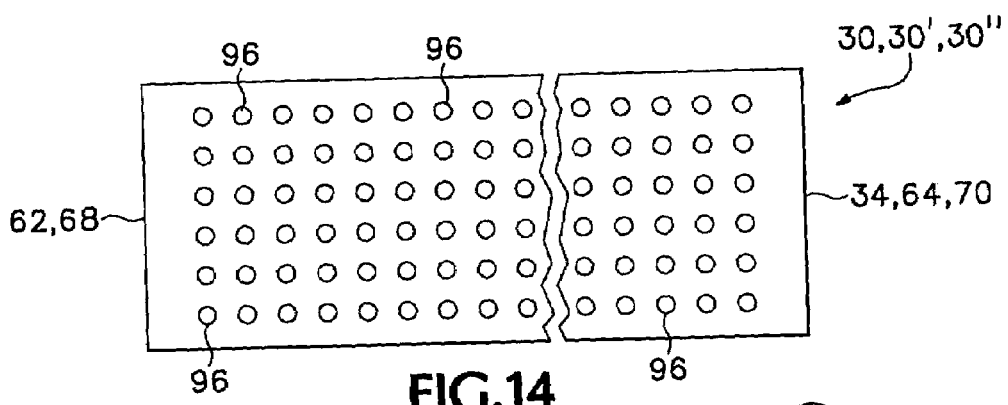
FIG. 14 is a plan view of a portion of another alternative core for a splint according to the present invention.

As shown in FIG. 14, the core 30, 30', or 30" may be perforated, providing ventilation through an array of holes 96. The holes 96 cooperate with the absorbent material of the closer face part 54 of the outer cover 52, and with the closer side layer 44 of padding material, to provide comfort by promoting ventilation and facilitating cooling and evaporation of perspiration from the patient's skin. When a perforated core is used, an open-cell foam similar to that described for use as the closer side layer 44 may also be used for the farther side layer 42.

Figure 15:
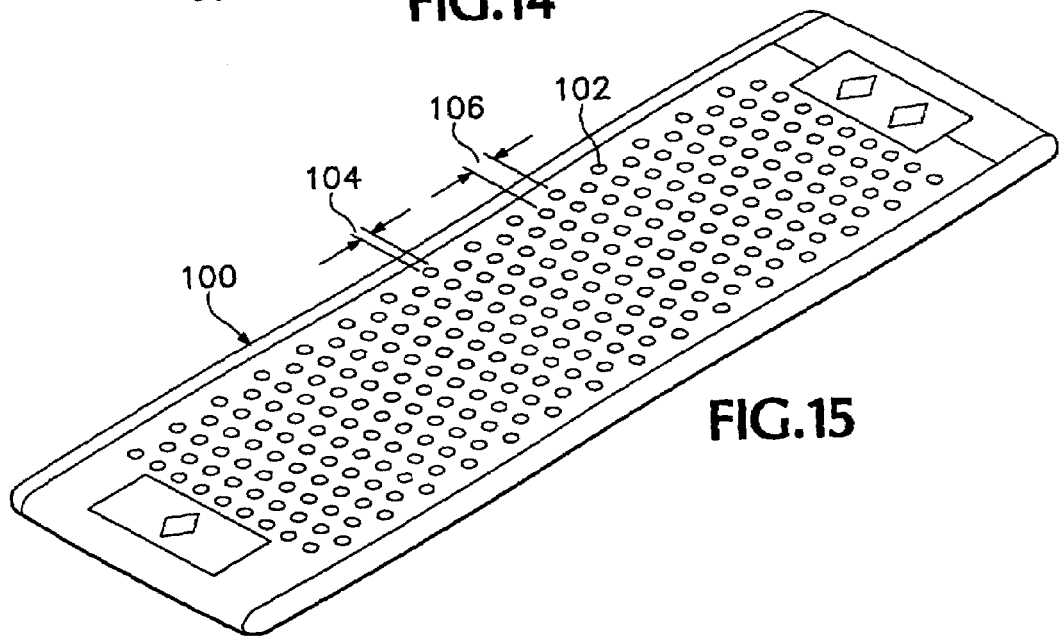
FIG. 15 is an isometric view of a splint including an alternative embodiment of the invention.

Referring to FIG. 15, a splint 100 is similar to the splint 12, except that it is perforated by holes 102, arranged in a regular pattern. The holes 102 may be circular, with diameters 104 in the range of 1/32 inch to 1/8 inch, for example, and spaced apart by a distance 106, of 1/2 inch to 1 inch, to provide comforting ventilation without significantly weakening the splint.

Referring now to FIGS. 16–23, an orthopedic splint 112 useful for support of an injured limb is similar in many respects to that of the splint 12 shown in FIGS. 1–13 and described above. The splint 112 is shown in FIG. 16 in a flat folded configuration convenient for packaging the splint 112 for storage or to be carried ready for use. A first, or inner face of the splint 112 is substantially hidden in FIG. 16, while a second, or outer face 114 faces outward when the splint is folded in the configuration shown in FIG. 16. Thus conveniently packaged, the splint 112 can be kept ready for use in hospital emergency rooms, medical clinics, or by athletic trainers, and can be carried conveniently in emergency vehicles, by search and rescue teams, or by military medical care teams.

As shown in FIGS. 17 and 18, the splint 112 is laid out at full length and flat, as by moving the end portion 118, one of a pair of opposite first and second end portions 116 and 118, away from the end portion 116 as shown by the arrow 119. The end portions 116, 118 are separated from and interconnected with each other by a central portion 120. The splint 112 has a length 122 which may, for example, be in the range of 24 inches to 43 inches overall, and preferably is in the range of about 30 inches to 40 inches, and most preferably about 37 inches. Each of the first and second end portions 116, 118 includes a respective core 124, 126, and the central portion 120 is located between the cores 124, 126. The cores 124, 126 are preferably of malleable metal in the form of a flat sheet, such as the aluminum used for the core 30 in the splint 12, and each of the cores 124, 126 may be of uniform thickness throughout its entire length 128. The length 128 of each of the cores 124 and 126 may be in the range of about 10 to 18 inches and is preferably about 16 inches. Each may have a thickness 130 in the range of 0.014–0.035 inch, and may preferably have a thickness 130 of about 0.016 inch. If desired, each core 124, 126, or the entire splint could be perforated as is the core 30 shown in FIGS. 14 and 15, by small holes 131, to provide improved breathability and comfort.

The central portion 120 has a length 132 which may be in the range of about 4 inches to about 9 inches and is preferably about 7 inches. The splint 112 has a width 134 which may be in the range of about 2.5 to 6 inches and preferably is about 4.5 inches, while each of the cores 124 has a width 136 somewhat less than the width 134. As with the wrist splint 12, the width 136 of each core 124 of 126 may, for example, be about 0.5 inch to 0.8 inch less than the width 134 of the splint 112.

The structure of the splint 112 in each of the first and second end portions 116 and 118 is similar to that of the splint 12. Attached to a first side of the respective core 124, 126 in each of the first end and second end portions 116, 118 is a first layer 140 of flexible and resilient padding material that extends over the entire length 122 of the splint 112. The first layer 140 of padding material is attached to the first side of each of the cores 124 and 126 by a thin layer 148 of an adhesive material and extends over the length 132 of the central portion 120.

On the second side of each of the first and second end cores 124 and 126, a second layer 142 of flexible and resilient padding material also extends over the entire length 122 of the splint 112 and is attached by a layer 150 of adhesive material to both the core 124 and the core 126. The second layer 142 also extends over the entire length 132 of the central portion 120, within which the first and second layers 140, 142 of padding material are located closely alongside and parallel with each other, attached to each other by the layers 148, 150 of adhesive material.

As in the splint 12, the layers 140 and 142 of padding material extend laterally and longitudinally beyond the margins of the cores 124 and 126 by a distance sufficient to provide some comfortable padding of those margins and to permit the layers 140 and 142 to be interconnected securely to each other by the adhesive material of the layers 148 and 150.

The central portion 120 may optionally be shaped, preferably along a smoothly curved margin 151 shown in FIG. 17, to be narrower than the end portions 116 and 118, to provide increased freedom of movement of the end portions 116, 118 relative to each other.

The first layer 140 of padding material has a preferred thickness 144 of about 1/4 inch, although a thickness in the range of 1/8 inch to 3/8 inch is acceptable. The first layer 140 of padding material is preferably resiliently compressible and porous and may preferably be of material similar to that described above with respect to the layer 44 of padding material in the splint 12.

The second layer 142 of padding material has a thickness 146, preferably in the range of 1/16 inch to 1/4 inch, and most preferably about ⅛ inch. The second layer 142 is preferably of a resiliently compressible or elastomeric polymeric material such as a closed cell microcellular low density expanded polyethylene foam and may be of the same material described above with respect to the farther side layer 42 of padding material for the splint 12.

The first and second layers 140, 142 of padding materials when adhesively fastened together are resiliently compressible, soft, flexible, and elastic enough to permit the central portion 120 of the orthopedic splint 112 to be bent easily to conform to the shape of a patient's elbow and upper arm in use of the splint 112.

Although the splint could be used without it, a cover 152 preferably fits snugly and smoothly over the layers of padding material. Because of a snug fit and the normal friction between open-cell foam surfaces and cloth, the cover 152 need not usually be fastened by an adhesive, but a suitable adhesive such as a thermally activated fabric adhesive film or a suitable spray-on adhesive may be used if desired. The cover 152 is preferably made of two different types of material, of which the material of the outer face 114 may be a smooth, soft, and strong material such as tricot, and which may be similar to the material used for the farther face part 56 of the outer cover 52 of the wrist splint 12, and which may, if desired, be of a type that is receptive to the small hooks of a hook-and-loop fastener material. Preferably, the outer face 114 is of material also receptive to screen printing of labels or instructions for use. An inner face portion 154 of the cover 152 is preferably of a soft, flexible, and moisture-absorbent material such as a brushed terry cloth or a boucle fleece similar to the material described above with respect to the closer face part 54 of the outer cover 52 of the wrist splint 12. The material of the inner face 154 may extend around the lateral margins of the padding material to provide a narrow strip 156 along each lateral margin of the outer face 114, as shown in FIGS. 16 and 21.

As may be seen in FIGS. 17 and 18, the material of the inner face portion 154 of the cover 152 of the splint 112 lies alongside and is supported by the preferably thicker material of the first layer 140 of padding material, while the material of the outer face 114 portion of the cover 152 lies alongside and parallel with the thinner second layer 142 of padding material.

The splint 112 is used by shaping the end portions 116 and 118 to fit opposite sides of a patient's forearm F. This includes manually bending the cores 124 and 126 so that the inner faces 154 of the first and second end portions 116 and 118 are concave and face concavely inward toward each other resembling channels or partial cylinders to conform to the surface of the forearm F which is to be supported by the splint 112. The cylinder or channel shape adds rigidity to each end portion 116, 118 of the splint 112 to resist bending along its length. If the end portions 116, 118 of the splint are too long, their outer ends can be folded back so that they do not extend all the way to the patient's knuckles, before the end portions 116, 118 are bent into channels. The thicker first layer 140 of padding material faces toward the forearm F which is to be supported by the splint 112, as is shown in FIG. 22. The flexible central portion 120 of the splint is bent freely to fit snugly around and conform to the surface of the person's upper arm and elbow as shown in FIG. 21 and the first and second end portions 116, 118, appropriately shaped to conform to the forearm, are applied snugly to the forearm, preferably extending over the wrist and may be held in place by an elastic bandage 172, described below. Other fasteners, including strong adhesive tape such as an elastic self-adhesive laminated tape available from the 3M Company under the trademark COBAN™, elastic bands such as the straps 82 mentioned above in connection with the splint 12, or, one or more straps 160 shown in FIGS. 19 and 20 may be used to hold the splint 112 in place.

Hook-and-loop fastening material is incorporated in the straps 160 to retain the strap 160 in a loop configuration surrounding the splint 112 and a limb supported by it. For example, a strap 160 may have a length 162 in the range of about 14 inches to about 18 inches and a width of about 1 inch to about 3 inches for use together with the splint 112, with the length being, at a minimum, great enough to encircle a patient's forearm F and the splint 112 with sufficient overlap for engagement of a hook-and-loop fastening material to secure the strap to itself and, optionally, to the splint 112, as by engagement of a thistle-cloth, or hook, portion 166 of the fastening material into the outer face 114 of the splint, or into the terry cloth of the inner face portion and narrow strips 156 of the cover 152. To that end, the entire length of the strap may be of loop-equipped material of adequate strength, while a patch of hook material 166 having a length of about 1 to 5 inches, and preferably about 3 inches is included adjacent one end of the strap 160, as shown in FIG. 20.

When an elastic bandage 172 is snugly applied, flexibility of the central portion 120 permits the splint 112 to precisely conform to the unique anatomic shape of a patient's elbow without the bulky creases and uncomfortable stiff edges that would be formed by attempting to fold a splint containing a stiff central core in such a manner. In addition, precise conformation of the central portion 120 of the splint produced by snugly applying a bandage 172 strongly secures the flexible central portion 120 to the elbow and firmly fixes the supporting adjacent end portions 116, 118 of the splint 112, preventing their rotation about a central axis. This, in effect, provides better immobilization of the injured extremity, limiting pronation and supination of the wrist and forearm.

An elastic bandage 172 mentioned above and shown in FIG. 23 is one preferred wrapping used to secure the splint 112 in a desired position on a patient's forearm. Such an elastic bandage 172 may be of suitable soft elastic material such as is well known for elastic bandages, and may have a length 174 of, for example, about 60 to about 80 inches, and a width 176 of about 2 inches. A patch 178 of multiple hook fastener material having a length 180 of, for example, 1½ to 2 inches and having a width similar to the width 176 of the elastic bandage material may preferably be used to fasten the elastic bandage to the splint 112 and to secure it to itself to retain the splint 112.

Referring next to FIGS. 24, 25, and 26, a splint 184 is generally similar to the splint 112, although it is of a size better adapted for utilization to stabilize an injured patient's ankle or lower leg. For example, then, the overall length 186 of the splint 184 may preferably be in the range of 15 inches to 29 inches and is preferably in the range of about 17 to 25 inches and most preferably is about 23 inches. Each of the first and second end portions 188, 190 may have a length 192 in the range of about 7 inches to about 12 inches and preferably of about 10 inches, while the central portion 194 preferably has a length in the range from about 1½ inches to 4½ inches and preferably of about 3 inches. A pair of cores 198 of the end portions 188, 190, are preferably similar to each other and generally similar to the cores 124 and 126 of the end portions 116, 188 of the splint 112 described above. A width 200 of the splint 184 is preferably about 4½ inches, in a splint 184 intended for an adult's ankle, although it could be smaller for a splint intended for use with smaller patients. The width 201 and length 199 of each core 198 is slightly smaller than the corresponding length 192 and width 200 of the corresponding end portion 188 or 190 similar to the size relationships of the cores 124, 126 to the end portions 116, 118 of the splint 112.

The central portion 194 of the splint 184, as with the central portion 120 of the splint 112, is flexible, somewhat elastic, and compressible, and it is also shaped to be narrower, than the adjacent end portions 188 and 190, with concavely shaped lateral margins leaving a width 202 that at its narrowest point is preferably about 2½ inches. At least one and preferably each lateral margin of the central portion 194 is concave as shown at 204, so that unnecessary bulk is not included in the central portion 194 and the central portion can be bent to conform flexibly to the bottom of a patient's heel H and still fit within a patient's shoe or boot 206 when the splint 184 is applied to a patient's foot as shown in FIGS. 25 and 26. The central portion 194 supplies support and comfortable cushioning of the patient's foot within the boot 206, or between the foot and the ground, if swelling prevents use of the boot 206 or other available footwear.

In applying the splint 184, the core 198 of each of the end portions 188 and 190 is bent to conform the end portions 188 and 190 to the appropriate sides of the patient's ankle and lower leg L so that the splint provides adequate support, in the same manner in which the end portions 116 and 118 of the splint 112 are bent to conform to a patient's forearm. Straps 160, as shown in FIGS. 25 and 26 may be used to retain the splint 184 in position on patient's ankle and lower leg L. Such straps preferably have a length 162 of about 17 inches, plus or minus five inches, for use with the ankle splint 184, where the splinted foot can be placed in the patient's boot or shoe.

Should the boot or shoe not be supportive enough, it is preferred to secure the ankle splint 184 by use of a bandage 172 or the elastic adhesive tape mentioned above, to snugly and supportingly wrap the ankle splint 184.

A supportive shoe or boot, or firmly applied bandage 172, strongly secures the flexible central portion 194 to the heel and ankle and firmly fixes the connecting end portions 188, 190 of the splint 184. This prevents lateral and rotational movement but allows flexion and extension of the ankle.

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

What is claimed is:

1. An orthopedic splint, comprising:
   (a) an elongate body having opposite first and second end portions aligned end-to-end and a relatively flexible central portion extending between and interconnecting said end portions;
   (b) a respective elongate supporting core of malleable metal having a pair of opposite sides included in each of said end portions, said cores being manually bendable to a desired shape to provide support for opposite sides of a limb and being separated from each other by said relatively flexible central portion; and
   (c) a respective layer of flexible and resilient padding material covering each of said opposite sides of each said core, said central portion including an extension of at least one of said layers of padding material from said first end portion to said second end portion of said body.

2. The splint of claim 1 wherein each said core is of sheet metal having a uniform thickness.

3. The splint of claim 1 wherein said respective layers of padding material are attached to said cores by an adhesive.

4. The splint of claim 1 wherein a first said respective layer of padding material covers a first one of said opposite sides of one of said cores and is thicker than another said respective layer of padding material covering the other one of said pair of opposite sides of said one of said cores.

5. The splint of claim 4 wherein said first respective layer of padding material covering said first one of said pair of opposite sides of said core is of open-cell polymeric foam.

6. The splint of claim 4 wherein said respective layer of padding material covering said other one of said pair of opposite sides of said one of said cores is of open-cell polymeric foam.

7. The splint of claim 4 wherein said respective layer of padding material covering said other one of said pair of opposite sides of said one of said cores is of closed-cell polymeric foam.

8. The splint of claim 1 including an outer cover of a textile fabric enclosing said cores and said layers of padding material, and wherein said splint has a pair of opposite faces corresponding to said pair of opposite sides of each of said cores of said splint, and wherein said outer cover includes a first face portion that is of substantially elastically extensible fabric and defines a first one of said pair of opposite faces.

9. The splint of claim 8 wherein said elastically extensible fabric is moisture-absorbent.

10. The splint of claim 8 wherein said outer cover includes a second face portion defining a portion of said second one of said pair of faces of said splint, said second face portion of said outer cover being of material that is operatively receptive to engagement by a hook portion of a hook-and-loop fastener material.

11. The splint of claim 10 wherein said material of said second face portion is substantially inelastic.

12. The orthopedic splint of claim 1 wherein each of said respective layers of padding material extends along each of said cores and a respective portion of each of said respective layers of padding material is included in said central portion.

13. The orthopedic splint of claim 1, for use on an arm, wherein each of said cores has a length in the range of about 10 inches to 17 inches and said central portion has a length in the range of about 4 inches to about 9 inches.

14. The orthopedic splint of claim 1 wherein each of said end portions has a width in the range of about 3 inches to about 5 inches and said central portion has an equal width.

15. The orthopedic splint of claim 1 wherein each of said end portions has a width in the range of about 3 inches to about 5 inches and said central portion has a lesser width.

16. The orthopedic splint of claim 1, for use on an ankle, wherein each of said end portions has a length in the range of about 7 inches to 12 inches and said central portion has a length in the range of about 1½ inches to 4½ inches.

17. The orthopedic splint of claim 1 wherein said cores are generally planar and said splint is packaged for storage prior to use with said central section folded and said end portions alongside each other.

18. The splint of claim 1 wherein said central portion of said body is narrower than either of said first and second end portions thereof.

19. The splint of claim 1 wherein at least one said core is perforated.

* * * * *